United States Patent
Kim et al.

(10) Patent No.: US 12,234,598 B2
(45) Date of Patent: Feb. 25, 2025

(54) CLOTHES CARE APPARATUS

(71) Applicant: SAMSUNG ELECTRONICS CO., LTD., Suwon-si (KR)

(72) Inventors: Jee Yong Kim, Suwon-si (KR); Yong-Joon Jang, Suwon-si (KR); Sang Yeon Pyo, Suwon-si (KR); Hong Kwan Cho, Suwon-si (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 1045 days.

(21) Appl. No.: 17/257,963

(22) PCT Filed: Jul. 3, 2019

(86) PCT No.: PCT/KR2019/008117
§ 371 (c)(1),
(2) Date: Jan. 5, 2021

(87) PCT Pub. No.: WO2020/009464
PCT Pub. Date: Jan. 9, 2020

(65) Prior Publication Data
US 2021/0269965 A1    Sep. 2, 2021

(30) Foreign Application Priority Data
Jul. 5, 2018   (KR) .................. 10-2018-0078390

(51) Int. Cl.
*D06F 58/10*        (2006.01)
*A61L 9/20*         (2006.01)
(Continued)

(52) U.S. Cl.
CPC .............. *D06F 58/10* (2013.01); *A61L 9/205* (2013.01); *B01D 39/2068* (2013.01);
(Continued)

(58) Field of Classification Search
CPC .......... D06F 58/10; D06F 58/22; D06F 58/36; D06F 58/203; D06F 73/02; D06F 58/30;
(Continued)

(56) References Cited

U.S. PATENT DOCUMENTS

| | | | |
|---|---|---|---|
| 11,229,715 B2 | 1/2022 | Kim et al. | |
| 2003/0007905 A1* | 1/2003 | Tanaka | F01N 3/0222 |
| | | | 422/177 |
| 2014/0205504 A1* | 7/2014 | Khoshbin | B01J 19/123 |
| | | | 422/186.3 |

FOREIGN PATENT DOCUMENTS

| | | | |
|---|---|---|---|
| CN | 103643466 A | 3/2014 | |
| DE | 202006017471 U1 * | 3/2007 | ............... A61L 9/20 |

(Continued)

OTHER PUBLICATIONS

Translation KR-100807255-B1 (Year: 2008).*
(Continued)

*Primary Examiner* — Jessica Yuen
(74) *Attorney, Agent, or Firm* — STAAS & HALSEY LLP (57) ABSTRACT

A disclosed embodiment provides a clothes care device which can improve service life, is not influenced by humidity, and can resolve odor problems. A clothes care device, according to one aspect of the present invention, comprises: an air blower; a flow path through which air, which is made to flow by the air blower, moves; and a deodorizing module for purifying the air which is made to flow by the air blower. The deodorizing module comprises: a ceramic filter provided inside the flow path; and an ultraviolet light emitting unit provided on the outside of the flow path so as to face the ceramic filter.

17 Claims, 10 Drawing Sheets

(51) Int. Cl.
*B01D 39/20* (2006.01)
*B01D 46/00* (2022.01)
*B01D 46/44* (2006.01)
*D06F 58/22* (2006.01)
*D06F 58/36* (2020.01)

(52) U.S. Cl.
CPC ..... *B01D 46/0038* (2013.01); *B01D 46/0041* (2013.01); *B01D 46/44* (2013.01); *D06F 58/22* (2013.01); *D06F 58/36* (2020.02); *A61L 2209/12* (2013.01); *A61L 2209/14* (2013.01); *A61L 2209/15* (2013.01); *B01D 2239/045* (2013.01); *B01D 2279/55* (2013.01)

(58) Field of Classification Search
CPC .. A61L 9/205; A61L 2209/12; A61L 2209/14; A61L 2209/15; B01D 39/2068; B01D 46/0038; B01D 46/0041; B01D 46/44; B01D 2239/045; B01D 2279/55; B01D 39/2072; B01D 53/8668; B01D 53/885; B01D 46/10; B01D 2239/0471; B01D 2257/90; B01D 2259/804; B01D 2239/0258; B01D 2239/0478; B01D 2239/1241; B01D 2255/20707; B01D 2258/06; B01D 39/2093; Y02B 40/00
See application file for complete search history.

(56) References Cited

FOREIGN PATENT DOCUMENTS

| | | | | |
|---|---|---|---|---|
| EP | 1 602 774 | A1 | 12/2005 | |
| EP | 3 744 354 | A1 | 12/2020 | |
| GB | 2166758 | A * | 5/1986 | ......... B01D 39/2093 |
| JP | 10-57466 | A | 3/1998 | |
| JP | 2005-334617 | | 12/2005 | |
| JP | 2006-26507 | A | 2/2006 | |
| JP | 2006306633 | A * | 11/2006 | |
| KR | 100807255 | B1 * | 2/2008 | |
| KR | 20-0470268 | Y1 | 12/2013 | |
| KR | 10-2015-0087496 | | 7/2015 | |
| KR | 10-2016-0054734 | A | 5/2016 | |
| KR | 101796291 | B1 * | 11/2017 | |
| KR | 10-1796298 | | 12/2017 | |
| KR | 10-1796298 | B1 | 12/2017 | |
| KR | 10-2018-0056037 | | 5/2018 | |
| RO | 131897 | A2 * | 5/2017 | |

OTHER PUBLICATIONS

Translation DE-202006017471-U1 (Year: 2007).*
Translation RO-131897-A2 (Year: 2017).*
Translation RO-131897-A2 (Year: 2016).*
Translation, KR-101796291-B1 (Year: 2017).*
JPH0532039U and English Translation, Apr. 27, 1993 (Year: 1993).*
International Search Report dated Oct. 28, 2019, in corresponding International Patent Application No. PCT/KR2019/008117.
Xanyan, Yao et al.,: "Antibacterial performance of a novel photocatalytic-coated cordierite foam for use in air cleaners", Aug. 11, 2011 (Aug. 11, 2011), XP055825678.
Freyschlag, Cassandra G. et al: "Precious metal magic: catalytic wizardry", Materials Today, vol. 14, No. 4, Apr. 1, 2011 (Apr. 1, 2011), pp. 134-142.
Extended European Search Report dated Jul. 28, 2021, in European Application No. 19831294.4.
Office Action dated Oct. 13, 2023, in Korean Application No. 10-2018-0078390.
Office Action dated Apr. 27, 2023, in Korean Application No. 10-2018-0078390.
Office Action dated Jun. 7, 2023, in European Application No. 19 831 294.4.
Office Action dated Apr. 5, 2024, in European Application No. 19 831 294.4.

* cited by examiner

CLOTHES CARE APPARATUS

CROSS-REFERENCE TO RELATED APPLICATIONS

This application is a U.S. National Stage Application, filed under 35 USC 371, of International Application PCT/KR2019/008117, filed Jul. 3, 2019, and claims foreign priority to Korean Application No. 10-2018-0078390, filed Jul. 5, 2018, in the Korean Patent Office, the contents of both of which are incorporated herein by reference in their entireties.

TECHNICAL FIELD

The present disclosure relates to a clothes care apparatus including a ceramic filter.

BACKGROUND ART

A clothes care apparatus is a type of device performing clothes care, such as removing dust attached to clothes or eliminating remaining odors in the clothes and removing wrinkles from the clothes.

The clothes care apparatus includes a main body provided with a clothes care chamber in which clothes is placed and the clothes care is performed, and a door configured to open and close the clothes care chamber. In addition, the main body includes a blower configured to supply air or hot air to the clothes, and a steam generator configured to supply steam to the clothes.

Therefore, the clothes care apparatus serves to remove the dust or odors attached to the clothes from the clothes by supplying air or hot air generated by the blower to the clothes, and the clothes care apparatus servers to remove wrinkles formed on the clothes by spraying steam generated by the steam generator to the clothes.

DISCLOSURE

Technical Problem

The present disclosure is directed to providing a clothes care apparatus capable of being used semi-permanently, capable of easing an off-flavor difficulty, and capable of being not affected by humidity by independently configuring a ceramic filter having a mechanism of chemical decomposition.

Technical Solution

One aspect of the present disclosure provides a clothes care apparatus including a blower, a flow path through which air flowing by the blower moves, and a deodorization module configured to purify the air flowing by the blower. The deodorization module includes a ceramic filter provided inside the flow path, and an ultraviolet light emitter provided on an outside of the flow path to face the ceramic filter.

The deodorization module may further include a supporter configured to support the ultraviolet light emitter to be spaced apart from the ceramic filter by a predetermined distance.

The supporter may be formed of at least one material of Poly (methyl methacrylate), polycarbonate, FR4, glass, and aluminum.

The supporter may have a thickness of 1 mm to 2 mm.

The ceramic filter may include a base material formed of at least one of cordierite and mullite, and a catalyst applied on a surface of the base material.

The catalyst may include at least one of titanium oxide ($TiO_2$), tungsten oxide ($WO_3$), zinc oxide (ZnO), manganese dioxide ($MnO_2$), or titanium tetraisopropoxide (TTIP).

The catalyst may include at least one metal of Mn, Cu, Co, Pt, and Au.

The base material may be formed in a honey-comb type having 100 to 300 pixels per inch.

The base material may be formed in a porous foam type having 15 to 20 pixels per inch.

A distance between the ceramic filter and the ultraviolet light emitter may be 10 mm or more and 25 mm or less.

A thickness of the ceramic filter may be 5 mm or more and 15 mm or less.

The number of cells of the ceramic filter may be 200 or more and 800 or less.

The clothes care apparatus may further include a controller configured to adjust a current applied to the ultraviolet light emitter to a range from 50 to 200 mA.

The clothes care apparatus may further include a controller configured to adjust an operation time of the ultraviolet light emitter to a range of from 10 to 60 minutes.

The clothes care apparatus may further include a controller configured to adjust a current applied to the ultraviolet light emitter in accordance with an intensity of air volume of the blower.

The clothes care apparatus may further include a controller, in response to a second mode in which an intensity of air volume of the blower is stronger than a first mode, configured to increase a current value, which is applied to the ultraviolet light emitter, to a second current value greater than a first current value corresponding to the first mode.

The clothes care apparatus may further include a controller configured to adjust a current applied to the ultraviolet light emitter in accordance with a temperature of air introduced by the blower.

The clothes care apparatus may further include a controller configured to block a current applied to the ultraviolet light emitter in response to a temperature of air introduced by the blower being higher than 70° C.

The clothes care apparatus may further include a controller configured to adjust a flow rate of air passing through the ceramic filter to 0.5 to 3.0 m/sec.

The deodorization module may further include a dust collecting filter provided at a front end of the ceramic filter.

Advantageous Effects

The clothes care apparatus according to the disclosed embodiment increase the service life and ease the off-flavor difficulty by independently configuring the ceramic filter having a mechanism of chemical decomposition.

The clothes care apparatus may improve high temperature/high humidity reliability of ultraviolet light emitting diodes (UV-LEDs) by installing the UV-LEDs on the outside of the flow path.

BEST MODE OF THE INVENTION

One aspect of the present disclosure provides a clothes care apparatus including a blower, a flow path through which air flowing by the blower moves, and a deodorization module configured to purify the air flowing by the blower. The deodorization module includes a ceramic filter provided inside the flow path, and an ultraviolet light emitter provided on an outside of the flow path to face the ceramic filter.

MODES OF THE INVENTION

Like numbers refer to like components throughout this specification. This specification does not describe all components of the embodiments, and general information in the technical field to which the present disclosure belongs or overlapping information between the embodiments will not be described.

It will be understood that when the terms "includes," "comprises," "including," and/or "comprising," when used in this specification, specify the presence of a stated component, but do not preclude the presence or addition of one or more other components.

It is to be understood that the singular forms "a," "an," and "the" include plural referents unless the context clearly dictates otherwise.

It will be understood that when the terms "includes," "comprises," "including," and/or "comprising," when used in this specification, specify the presence of stated components, features, figures, steps, operations, or combination thereof, but do not preclude the presence or addition of one or more other components, features, figures, steps, operations, or combinations thereof.

The disclosure will be described more fully hereinafter with reference to the accompanying drawings.

Figure 1:
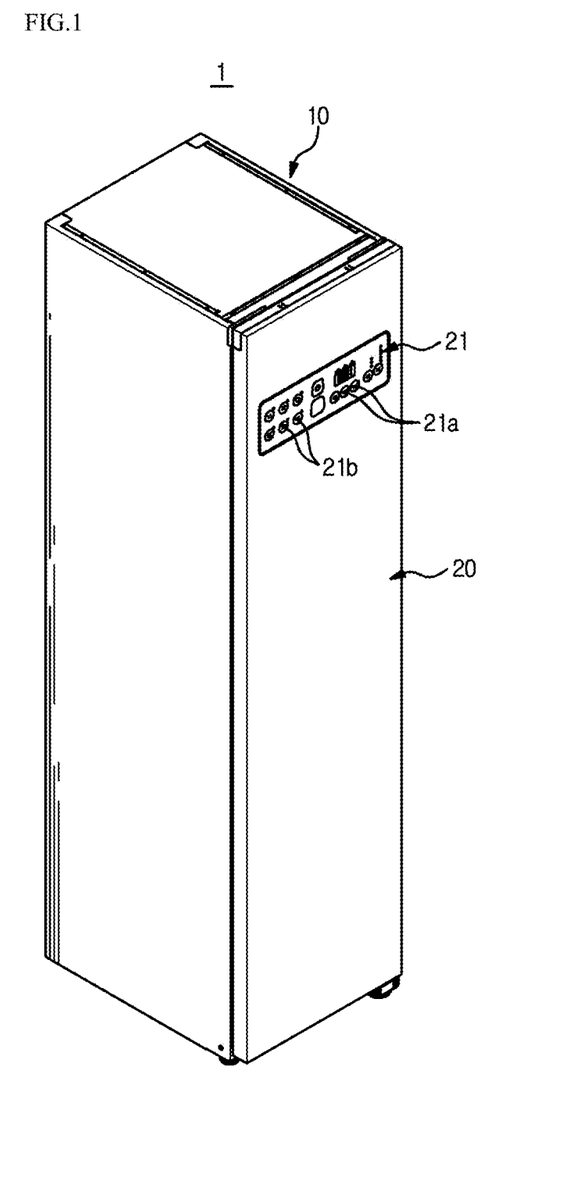
FIG. 1 is a perspective view of a clothes care apparatus according to one embodiment of the present disclosure.
Figure 2:
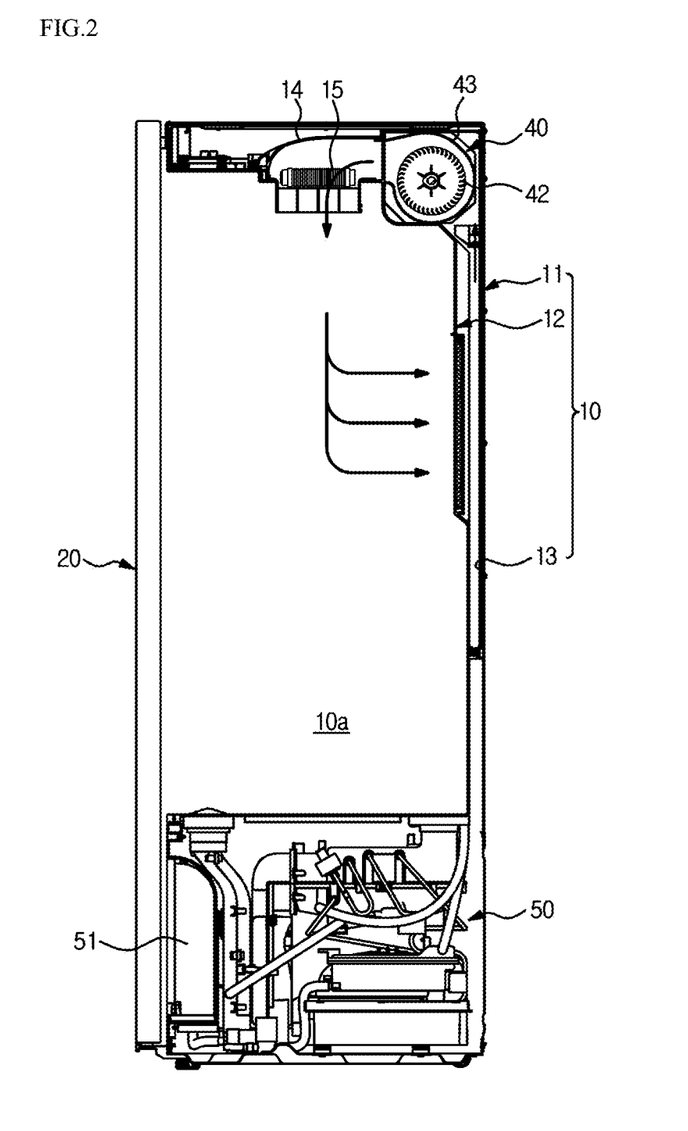
FIG. 2 is a side cross-sectional view of the clothes care apparatus according to one embodiment of the present disclosure.

FIG. 1 is a perspective view of a clothes care apparatus 1 according to one embodiment of the present disclosure, and FIG. 2 is a side cross-sectional view of the clothes care apparatus 1 according to one embodiment of the present disclosure.

Referring to FIGS. 1 and 2, the clothes care apparatus 1 according to one embodiment of the present disclosure may include a main body 10 including a clothes care chamber 10a in which clothes are accommodated and clothes care is performed, a door 20 configured to open and close the clothes care chamber 10a, a blower 40 provided above the clothes care chamber 10a and configured to supply air to the clothes care chamber 10a, a flow path along which air flowing from the blower 40 moves, and a deodorization module 30 configured to purify air flowing form the blower 40.

The clothes care apparatus 1 according to one embodiment of the present disclosure may further include a steam generator 50 provided in a lower portion of the main body 10 and configured to generate steam to be supplied to the clothes care chamber 10a. The main body 10 may include cooling cycle components for dehumidifying clothes, which are not clearly illustrated in the drawings.

Accordingly, in a state in which the clothes are placed in the clothes care chamber 10a, the dust or odors attached to the clothes may be removed from the clothes by supplying air generated by the blower 40 to the clothes care chamber 10a, and wrinkles formed on the clothes may be removed from the clothes by spraying steam generated by the steam generator to the clothes care chamber 10a.

Referring to FIG. 2, the main body 10 may include an outer housing 11, an inner housing 12 positioned inside the outer housing 11 to partition an inner space of the outer housing 11, and ducts 13 and 14 positioned between the outer housing 11 and the inner housing 12 to guide air to circulate.

One end of the door 20 may be rotatably mounted on one side of a front surface of the main body 10 and thus the door 20 may be rotatable to open and close the clothes care chamber 10a.

The door 20 includes a control panel 21 provided on the front surface of the door 20 to allow a user to select an operation of the clothes care apparatus 1. The control panel 21 may include various buttons 21a to allow a user to select an operation of the clothes care apparatus 1, and a display (or a touch screen) 21b on which an operation state of the clothes care apparatus 1 is displayed.

The button may be included in the display 21b or separated from the display 21b. The button may include a button displayed on the display 21b, a touch button, or a physical button. A clothes processing option (or menu) which is selectable by a user, an operating time, and a remaining time may be displayed on the display 21b.

The outer housing 11 may form an outer appearance of the main body 10, and may be in a shape of an enclosure that is elongated vertically. A front side of the outer housing 11 may be opened, and the inner housing 12, the blower 40, and the steam generator 50 may be accommodated in the inside of the outer housing 11.

Figure 3:
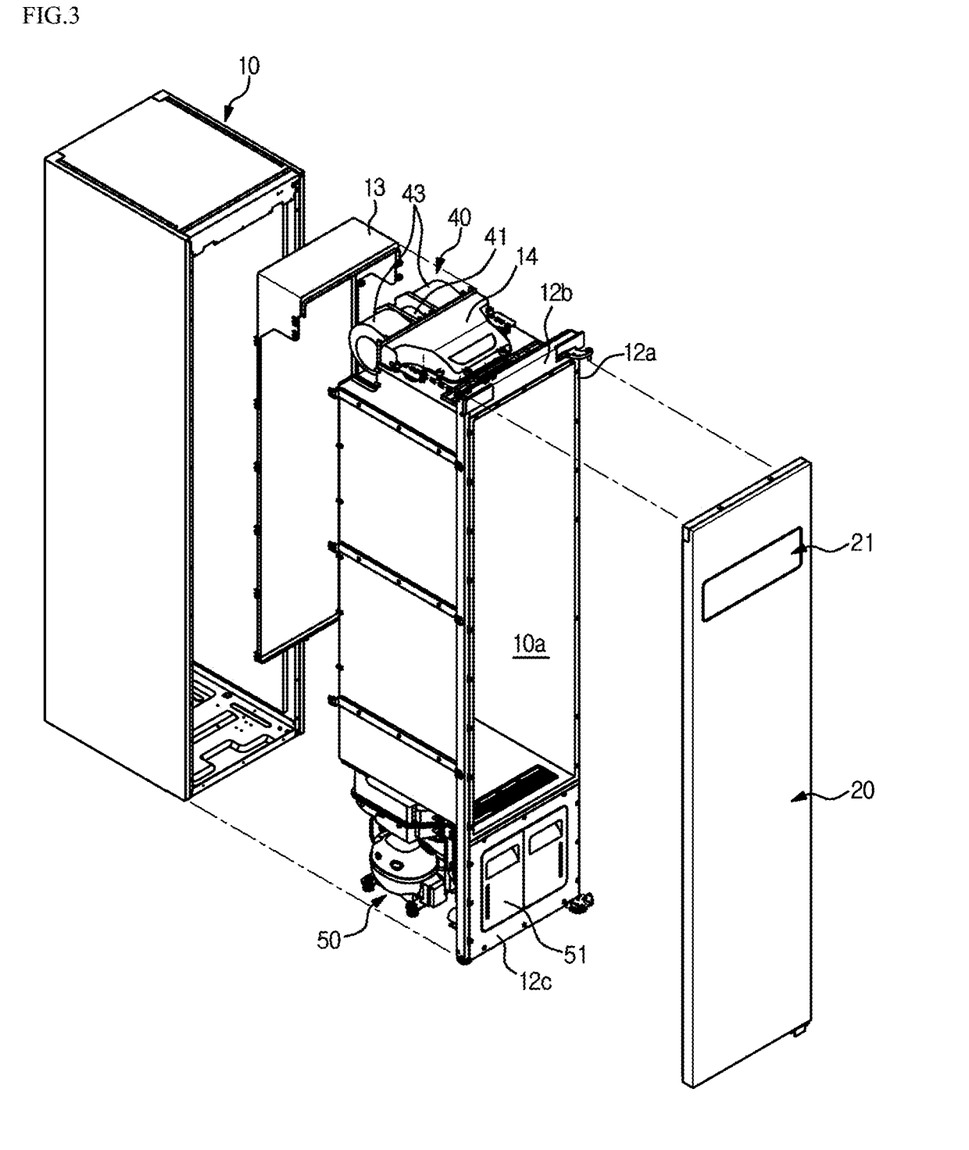
FIG. 3 is an exploded perspective view of the clothes care apparatus according to one embodiment of the present disclosure.

FIG. 3 is an exploded perspective view of the clothes care apparatus according to one embodiment of the present disclosure.

Referring to FIG. 3, the inner housing 12 includes a clothes care portion 12a formed in a shape of an enclosure with an open front side and configured to form the clothes care chamber 10a, a upper cover 12b extending upward from an upper end of a front surface of the clothes care portion 12a and configured to form a space in which the blower 40 is accommodated, and a lower cover 12c extending downward from a lower end of the front surface of the clothes care portion 12a and configured to form a space in which the steam generator 50 is accommodated.

Referring to FIGS. 2 and 3, the ducts 13 and 14 may include an inlet duct 13 configured to guide internal air of the clothes care chamber 10a to the blower 40, and an outlet duct 14 configured to disperse and guide air discharged from the blower 40.

Further, a heater 15 may be provided in a lower machine room, and some amount of air discharged from the heater 15 may be introduced into the inlet duct 13. The heater 15 may be installed in the outlet duct 14.

The inlet duct 13 may be installed in such a way that a lower portion of the inlet duct 13 is connected to a lower portion of a rear surface of the clothes care portion 12a, and an upper end of the inlet duct 13 covers the blower 40. The outlet duct 14 may be installed in such a way that a rear end of the outlet duct 14 is connected to the blower 40, and a front end of the outlet duct 14 covers an outer upper surface of the clothes care portion 12a.

Referring to FIG. 3, the blower 40 is installed in a rear side of an upper portion of the clothes care chamber 12a, and includes a drive motor 41 configured to generate a rotation force, two blowing fans 42 configured to be rotated by the drive motor 41, and a pair of fan cases 43 configured to respectively accommodate the two blowing fans 42.

A shaft of the drive motor 41 may extend at opposite sides thereof, and the two blowing fans 42 may be coupled to opposite ends of the shaft to be rotated simultaneously by the drive motor 41.

Each of the two blowing fans 42 may be a centrifugal fan configured to suction air in an axial direction and discharge the air outward in a radial direction.

The fan cases 43 may include an inlet (not shown) at opposite sides thereof and an outlet at a front side thereof and thus to guide air, which is suctioned from the opposite sides, to the front direction.

The steam generator 50 may include a water tank 51 configured to store water and a heater (not shown) configured to heat water to generate steam. The water tank 51 may be separable from the lower cover 12c. The steam generated by the steam generator 50 may be supplied to the clothes care chamber 10a through a hot air supply fan (not shown).

A conventional deodorizing device is provided with activated carbon provided at a front end thereof and configured to adsorb introduced gas and odor particles, and a support configured to support the activated carbon. A flow path of air may be moved to a vertical plane of the deodorizing device.

The conventional deodorizing device needs to replace a filter with a new one upon completion of adsorption because a physical adsorption method using activated carbon is used, and thus has a short replacement cycle. Further, the off-favor occurs because the life cycle thereof ends when an amount of adsorption reaches a break-through point. Further, activated carbon has strong moisture adsorption, and thus when using the activated carbon for the clothes care apparatus using steam, performance degradation rapidly occurs and an amount of steam attached to clothing is reduced.

Figure 4:
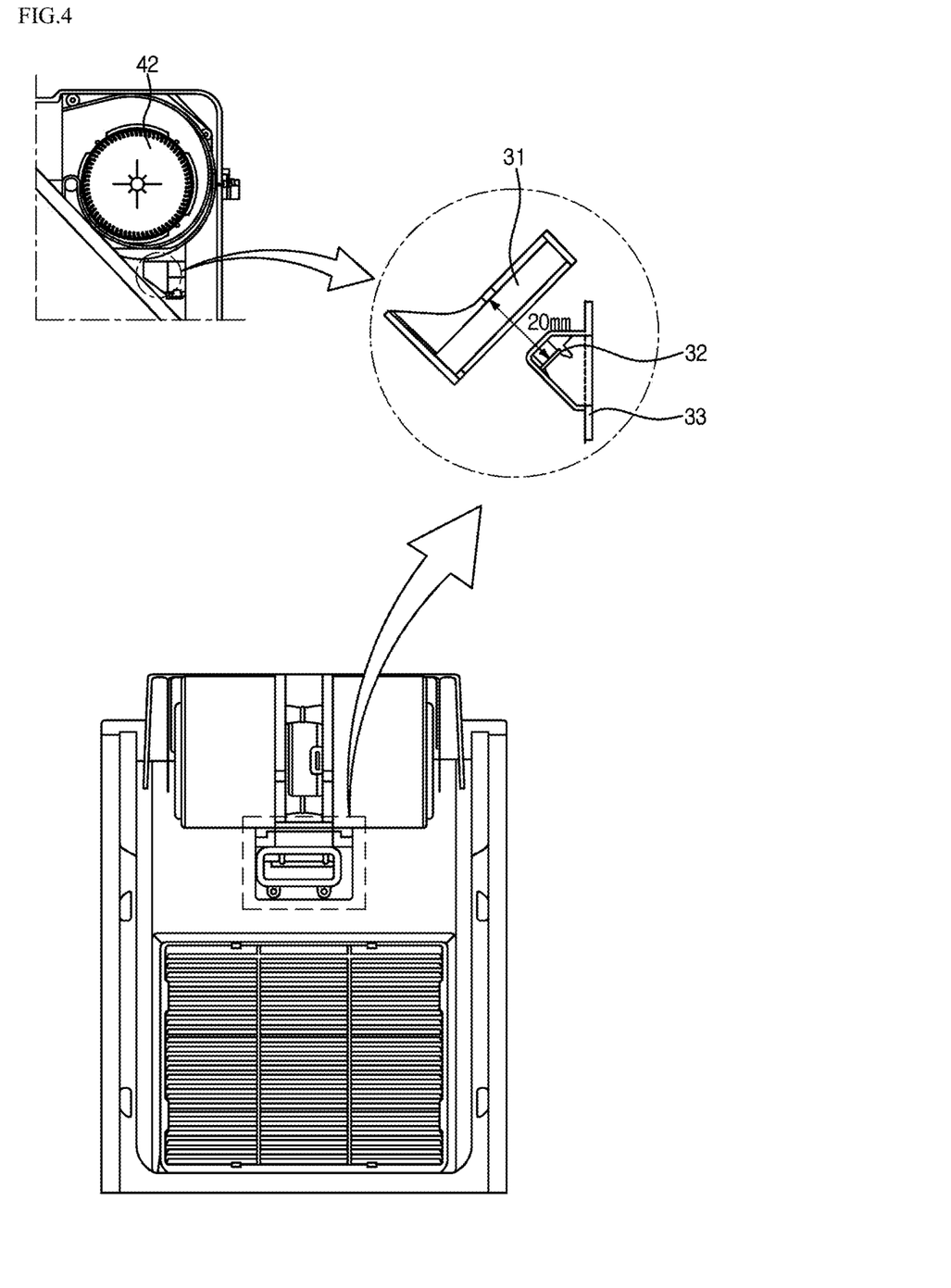
FIG. 4 is a view illustrating a deodorization module of the clothes care apparatus according to one embodiment of the present disclosure.

FIG. 4 is a view illustrating the deodorization module 30 of the clothes care apparatus 1 according to one embodiment of the present disclosure.

Referring to FIG. 4, the deodorization module 30 according to one embodiment of the present disclosure may be installed between the opposite inlets of the blower 40 installed in an upper portion of the rear side of the clothes care apparatus. Particularly, the deodorization module 30 may use ½ to ¼ of an entire area of the flow path to minimize flow resistance so as to maintain airflow.

The deodorization module 30 may include a ceramic filter 31 installed inside the flow path, and an ultraviolet light emitter 32 installed on the outside of the flow path to face the ceramic filter 31 so as to emit ultraviolet light to the ceramic filter 31.

Further, the deodorization module 30 may further include a dust collecting filter configured to collect gas and odor particles in air. The dust collecting filter may be positioned in front of the ceramic filter 31 to prevent contamination by lint. In addition, the dust collecting filter may be positioned at the opposite outlets of the blower 40.

The ceramic filter 31 may include a base material and a catalyst applied on a surface of the base material.

The base material of the ceramic filter 31 according to the disclosed embodiment may be implemented as a composite ceramic material for stabilization of catalyst coating. For example, the base material of the ceramic filter 31 may be implemented as Cordierite or Mullite composed of Alumina and Silica or as a combination of Cordierite and Mullite.

Meanwhile, a density and moisture content of the base material may be factors influencing impact strength and catalyst coating strength. Accordingly, by considering the impact strength and catalyst coating strength, a density of the base material may be 0.5 g/ml to 3.0 g/ml and a moisture content of the base material may be 5% or less.

Figure 5:
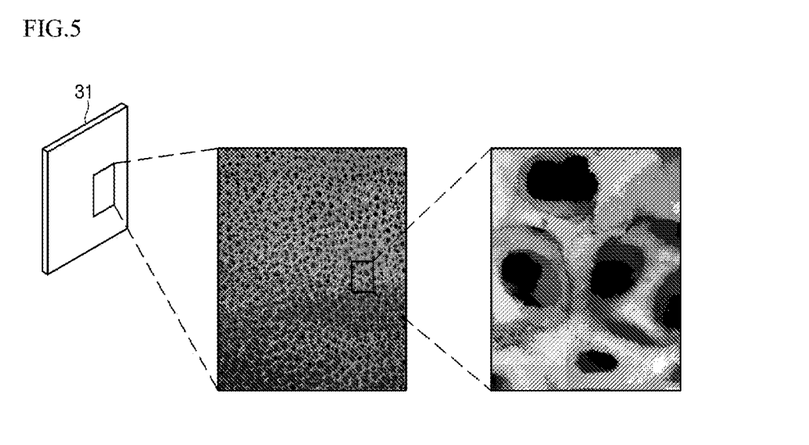
FIGS. 5 and 6 are enlarged-photographs illustrating a ceramic filter of the clothes care apparatus according to one embodiment of the present disclosure.
Figure 6:
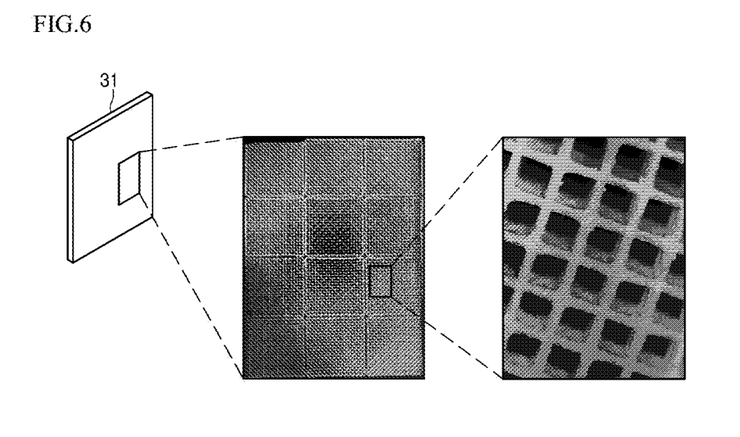

FIGS. 5 and 6 are enlarged-photographs illustrating the ceramic filter 31 of the clothes care apparatus 1 according to one embodiment of the present disclosure.

As illustrated in FIG. 5, the base material may be implemented as a porous foam type plate including irregular holes.

Alternatively, as illustrated in FIG. 6, the base material of the ceramic filter 31 may be implemented as a honey-comb type plate.

Particularly, the porous foam type base material may have 15 to 20 pixels per inch (ppi), and the honey-comb type base material may have 100 to 300 pixels per inch (ppi).

A shape of the ceramic filter 31 illustrated in FIGS. 5 and 6 may be an example, but it does not limit a shape of the base material of the ceramic filter 31.

According to an aspect of the present disclosure, the ceramic filter 31 may be formed by applying a photocatalyst, which is regenerated by light, on the base material, and thus according to the disclosed embodiment, the photocatalyst may include at least one of titanium oxide ($TiO_2$), tungsten oxide ($WO_3$), zinc oxide (ZnO), manganese dioxide ($MnO_2$), or titanium tetraisopropoxide (TTIP).

The photocatalyst may be coated on a surface of the base material by various methods. For example, the photocatalyst may be coated by a method, such as a spray method, and an impregnation method. However, the spirit of the disclosure is not limited to the above mentioned coating method, and a catalyst layer may be formed on the surface of the base material by well-known techniques.

The coated photocatalyst may not include a material such as $SiO_2$, and may be composed of only pure semiconductor metal. The reason is because a photocatalyst including an additional material may cause fouling.

In addition, a particle size of the coated photocatalyst may be 15 to 50 nm, appropriately, 20 to 40 nm. A photocatalyst having a particle size of 15 nm or less is inefficient in terms of production yield and coating stabilization, and requires a lot of energy due to an increase in band-gap energy. Further, a thickness of a coating film of the photocatalyst may be 100 nm to 4 μm, appropriately, 1 to 3 μm.

In the case of a photocatalyst of $TiO_2$, electrons in a valence band may be excited upon irradiation of ultraviolet light by the ultraviolet light emitter 32 and the electrons may be moved to a conduction band and thus holes may be generated in the valence band. In the case of $TiO_2$ having band-gap energy of 3.2 eV, when energy exceeding the band-gap energy is absorbed upon irradiation of ultraviolet light, electrons are excited and holes are generated as described above.

The electrons and holes react with oxygen and moisture in air to generate oxide ions and hydroxyl radicals, and the oxide ions and hydroxyl radicals oxidize various kinds of germs, viruses, or organic compounds to chemically decompose the germs, viruses, or organic compounds, thereby decomposing and removing odor and harmful materials remaining on the clothes.

Particularly, the photocatalyst may remove organic chloride compounds, volatile hydrocarbon, aldehyde, ketone, alcohol, phenols, ammonia, hydrogen sulfide, nitrogen oxides, sulfur oxides, etc. to perform the clothes care.

$TiO_2$ of photocatalyst materials has three types of crystal phases of a rutile structure, an anatase structure, and a brookite structure. Performance differences may be made according to portions of the structures, and in the disclosure, a ceramic filter including 50% of the anatase structure may be formed.

Meanwhile, in the case in which the clothes care apparatus 1 has a steam or drying function and accordingly has an internal temperature of 50° C. or higher, the clothes care apparatus 1 may be operated without the ultraviolet light emitter.

Accordingly, a ceramic filter 31 according to another aspect of the present disclosure may be formed by applying a thermal catalyst, which is generated by heat, on a base material.

The thermal catalyst according to one embodiment of the present disclosure may include at least one metal of Mn, Cu, Co, Pt, and Au.

Various metal oxide catalysts may be implemented based on the above-mentioned metal. As for metal oxide catalysts, as a crystal structure is increased and the number of bonded oxygen atoms is increased, it tends to have higher activation energy.

Mn oxide catalysts according to an aspect of the present disclosure may contain Mn 40% by weight or more, and the number of oxygen atoms boned to one Mn metal atom may be four or less.

For example, the Mn oxide may be at least one oxide selected from a group consisting of $MnO_2$, $Mn(O,OH)_2$, $Ba_x(Mn^{4+},Mn^{3+})_8O_{16}$, $K_x(Mn^{4+},Mn^{3+})_8O_{16}$, $Na_x(Mn^{4+},Mn^{3+})_8O_{16}$, $Pb_x(Mn^{4+},Mn^{3+})_8O_{16}$, $Ba_{0.66}(Mn^{4+},Mn^{3+})_5O_{10} \cdot 1.34H_2O$, $(Ca,Na,K)_x(Mn^{4+},Mn^{3+})_6O_{12} \cdot 3.5H_2O$, $LiAl_2(Mn_2^{4+},Mn^{3+})O_6(OH)_6$, $ZnMn_3O_7 \cdot 3H_2O$, $(Na,Ca)Mn_7O_{14} \cdot 2.8H_2O$, $MnO_2 \cdot nH_2O$, $MnOOH$, $Mn^{2+}Mn_2^{3+}O_4$, $Mn_2O_3$, $Mn(OH)_2$, and $MnO$.

A particle size of coated metal oxide catalysts may be 100 nm to 2 μm.

Further, a coating film thickness of the thermal catalyst may be 5 or less, appropriately, 1 to 3 μm.

The thermal catalyst may be coated on the surface of the base material by various methods. For example, the thermal catalyst may be coated by a method, such as a spray method, an impregnation method, etc. However, the spirit of the disclosure is not limited to the coating method, and a catalyst layer may be formed on the surface of the base material by various known techniques.

The catalyst according to one embodiment of the present disclosure may be regenerated by light or heat, and recombination and oxidation-reduction reactions between hole-electron pairs may competitively act, thereby chemically decomposing harmful materials or odor particles. Therefore, the clothes care apparatus 1 may implement deodorization technology without requiring filter replacement.

FIG. 4 is a view illustrating a deodorization module of the clothes care apparatus according to one embodiment of the present disclosure. Referring to FIG. 4, the ultraviolet light emitter 32 may be positioned on the outside of the flow path to face the ceramic filter 33.

The ultraviolet light emitter 32 may include a plurality of ultraviolet light emitting diodes (UV-LEDs) configured to emit ultraviolet light having a UV-A wavelength range of 315 to 400 nm. The light emitted from the UV-LEDs may be irradiated to the ceramic filter 31 through a transparent injection molded material or glass.

Particularly, the UV-LEDs may emit ultraviolet light having a main wavelength range of 360 to 370 nm, and have an irradiation angle of 100° or more. Appropriately, an irradiation angle may be 110° or more.

A diameter of each UV-LED may be 5 or less and a height of each UV-LED may be 2.5 mm.

A printed board assembly (PBA) of the ultraviolet light emitter 32 may be provided with one or more resistors or constant current integrated circuits (ICs) to maintain an applied current value. Particularly, a capacity of the resistors or constant current ICs may be from 0.5 to 3 W in consideration of the range of fluctuation of a used current value and an applied voltage. In addition, a distance from the resistors or constant current ICs to the UV-LEDs may be 2 mm or more.

A size of the PBA of the ultraviolet light emitter 32 may need to be minimized in consideration of flow resistance in a state of being installed in a rear duct. In the disclosure, the size of the PBA may be optimized to 67 mm*10 mm to minimize the flow resistance.

The deodorization module according to an aspect of the present disclosure may further include a supporter 33 configured to support the ultraviolet light emitter 32 to be spaced apart from the ceramic filter 31 by a predetermined distance.

In this case, ultraviolet light may be irradiated to the ceramic filter 31 through the supporter 33 which is transparent.

The supporter 33 may support the ultraviolet light emitter 32 to be spaced apart from the ceramic filter 31 by the predetermined distance. Particularly, the ultraviolet light emitter 32 may be positioned behind the supporter 33, as shown in FIG. 4, so as not to be in direct contact with a flowing material. The supporter 33 may be positioned in such a way that a distance between the ceramic filter 31 and the ultraviolet light emitter 32 is 10 to 30 mm.

The supporter 33 may have a thickness of 1 to 2 mm by considering ultraviolet irradiation efficiency, and may be formed of at least one material of Poly(methyl methacrylate), polycarbonate, glass-reinforced epoxy laminate material (FR4), glass, and aluminum to be transparent.

As illustrated in FIG. 4, the ultraviolet light emitter 32 may be positioned on the outside of the flow path by the supporter 33, so as not to be in direct contact with air, thereby improving high-temperature/high-humidity reliability.

Hereinafter current values applied to the ultraviolet light emitter, sizes of the ceramic filter and flow rates of air passing through the ceramic filter will be described in consideration of efficiency of photocatalyst.

Figure 9:
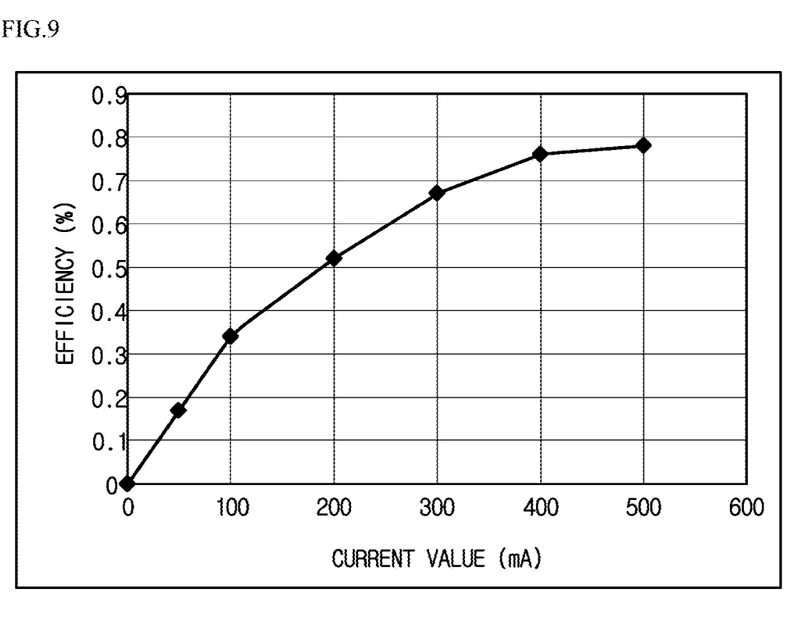
FIG. 9 is a graph illustrating a correlation between a current value applied to an ultraviolet light emitter and efficiency of photocatalyst.

FIG. 9 is a graph illustrating a correlation between a current value applied to an ultraviolet light-emitter and efficiency of photocatalyst.

Referring to FIG. 9, efficiency of photocatalyst according to one embodiment of the present disclosure may be improved as a current value applied to the ultraviolet light emitter 32 is increased. Particularly, the efficiency of the photocatalyst may be increased consistently until a current value applied to the ultraviolet light emitter 32 reaches 500 mA. However, an increase in the efficiency may be saturated due to recombination of electrons in a current range over 500 mA. Further, in the disclosure, a range of current values applied to the ultraviolet light emitter 32 may be set to from 50 to 200 mA in consideration of a life cycle of the UV-LEDs.

Meanwhile, a current value applied to the ultraviolet light emitter 32 may be affected by an area of the ceramic filter 31 and a distance between the ceramic filter 31 and the ultraviolet light emitter 32.

As the area of the ceramic filter 31 is increased, a distance between the ceramic filter 31 and the ultraviolet light emitter 32 may need to increase, which causes an increase in a current value applied to the ultraviolet light emitter 32.

The following Table 1 shows minimum/maximum values of current values applied to the ultraviolet light emitter 32 according to areas of the ceramic filter 31.

TABLE 1

| Area of Ceramic Filter | Distance Between Ceramic Filter and Ultraviolet Light Emitter | Current Value | |
|---|---|---|---|
| $Cm^2$ | mm | Min | Max |
| 6.25 | 10.0 | 41 mA | 90 mA |
| 30.25 | 20.0 | 90 mA | 200 mA |
| 64 | 30.0 | 135 mA | 300 mA |
| 121 | 40.0 | 180 mA | 400 mA |

Referring to Table 1, by considering saturation of efficiency of ceramic catalyst according to current values, an area of the ceramic filter 31 may be appropriately 121 $cm^2$ or less.

Further, a distance between the ceramic filter 31 and the ultraviolet light emitter 32 may be appropriately 10 to 25 mm in consideration of a range of current values applied to the ultraviolet light emitter 32.

Generally, as irradiance is increased, the efficiency is increased, but in a range of 40 $mW/cm^2$ or more, an effect of the increase of the efficiency is insignificant. The irradiance may be inversely proportional to the area of the ceramic filter 31. Accordingly, in the disclosure, after a range of irradiance is set to 5 to 15 $mW/cm^2$, a distance between the ceramic filter 31 and the ultraviolet light emitter 32 is deduced according to the area of the ceramic filter 31.

Accordingly, in response of a current value of 200 mA applied to the ultraviolet light emitter 32, an optimal distance between the ceramic filter 31 and the ultraviolet light emitter 32 may be deduced as 20 to 25 mm through light distribution analysis according to an area of the ceramic filter 31.

Figure 8:
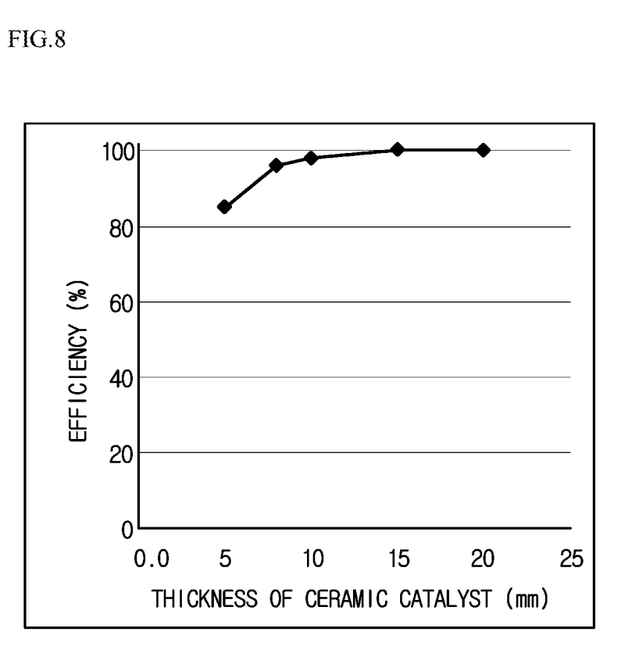
FIG. 8 is a graph illustrating a correlation between a thickness of the ceramic filter and efficiency of photocatalyst.

FIG. 8 is a graph illustrating a correlation between a thickness of the ceramic filter and efficiency of photocatalyst.

Referring to FIG. 8, efficiency of photocatalyst according to one embodiment of the present disclosure may be improved as a thickness of the ceramic filter 31 is increased. Particularly, the efficiency of the photocatalyst may be increased consistently in a thickness range of from 5 to 15 mm of the ceramic filter 31. However, in the thickness range over 15 mm, the increase in the efficiency may be saturated due to an increase in the flow resistance.

Accordingly, in the disclosure, the thickness of the ceramic filter 31 may be set to the range of from 5 to 15 mm in consideration of flow characteristics and efficiency. However, in the case of increasing a light amount of the ultraviolet light emitter 32, the ceramic filter 31 having a thickness of 20 mm or less is applicable.

Further, the efficiency of the photocatalyst may be affected by the number of cells of the ceramic filter 31.

The following Table 2 shows resistances, performances, and flow-through rates according to the numbers of cells of the ceramic filter 31.

TABLE 2

| Number of Cells (55 mm * 55 mm) | Resistance (mmAq, @1 m/sec) | Performance (%) | Flow-Through Rates (m/sec) |
|---|---|---|---|
| 200 cell | 0.08 | 85 | 2.0 |
| 400 cell | 0.2 | 95 | 1.6 |
| 800 cell | 0.4 | 100 | 1.3 |

Referring to Table 2, as the number of cells is increased, the efficiency of the photocatalyst is increased, and resistance is also increased. Accordingly, the number of cells of the ceramic filter 31 may be appropriately 200 to 800 in consideration of the resistance and the efficiency.

Figure 7:
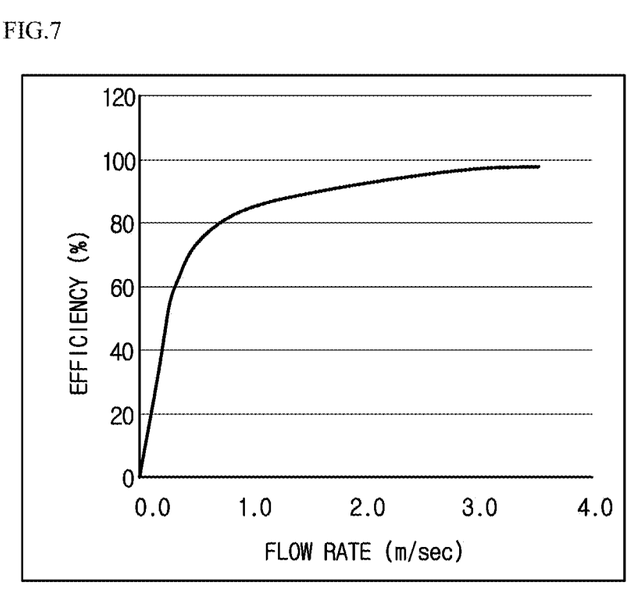
FIG. 7 is a graph illustrating a correlation between a flow rate of air passing through the ceramic filter and efficiency of photocatalyst.

FIG. 7 is a graph illustrating a correlation between a flow rate of air passing through the ceramic filter and efficiency of photocatalyst.

Referring to FIG. 7, a flow rate of air passing through the ceramic filter 31 may be appropriately 0.5 to 3.0 m/sec in consideration of the efficiency of the photocatalyst of 80% or more and saturation of the efficiency increase. In consideration of noise, the flow rate of air passing through the ceramic filter 31 may be more appropriately 1.0 to 2.0 m/sec.

As described above, for the efficiency of the photocatalyst, the current value applied to the ultraviolet light emitter 32 and the flow rate of air passing through the ceramic filter 31 may need to be controlled. Accordingly, the clothes care apparatus according to another aspect of the present disclosure may further include a controller (not shown).

The controller may control driving of the ultraviolet light emitter 30 or the blower 40 based on data about air volume of the blower 40 input through an inputter or a temperature of air introduced by the blower 40.

Further, the controller may control driving of the ultraviolet light emitter 30 or the blower 40 according to a user input received through an inputter and a temperature of air detected by an air sensor.

The controller may control overall operations of the clothes care apparatus, and it may be interpreted that operations of the clothes care apparatus, which will be described blow, is performed by the control of the controller.

As described above, the controller may adjust a range of a current value applied to the ultraviolet light emitter 32 to from 50 to 200 mA in consideration of the efficiency of the photocatalyst.

Further, the controller may adjust the blower 40 to allow a flow rate of air passing through the ceramic filter 31 to be 0.5 to 3.0 m/sec in consideration of the efficiency of the photocatalyst.

In addition, the clothes care apparatus according to the disclosed embodiment may control a current value applied to the ultraviolet light emitter 32 according to a change in an intensity of the air volume of the blower 40, thereby adjusting performance of the ceramic filter 31.

Particularly, in response to a command, which is to change the air volume of the blower 40 from a first mode to a second mode, that is, a command to increase the air volume of the blower 40, being input through the inputter, the controller may increase a current value applied to the ultraviolet light emitter 32.

The first mode and the second mode are relative concepts, and the first mode is a mode in which the blower 40 generates weaker air volume than in the second mode, and the second mode is a mode in which the blower 40 generates stronger air volume than in the first mode. For example, when the first mode is a so-called weak mode, the second mode may be a so-called medium mode or a so-called strong mode or when the first mode is a medium mode, the second mode may be a strong mode. Likewise, when the second mode is a strong mode, the first mode may be a weak mode or a medium mode or when the second mode is a so-called medium mode, the first mode may be a weak mode.

In response to receiving a command to change the first mode to the second mode, the controller may increase a first current value, which is applied to the ultraviolet light emitter 32 in accordance with the first mode, to a second current value, which is applied to the ultraviolet light emitter 32 in accordance with the second mode. For example, the controller may apply a first current value of 50 mA to the ultraviolet light emitter 32 in the first mode, and in response to changing the first mode to the second mode, the controller may apply a current, which is increased to a second current value of 200 mA, to the ultraviolet light emitter 32.

As the air volume of the blower 40 is increased, an amount of external air introduced per a reference time is increased. Therefore, it is difficult to satisfy air purification performance of the ceramic filter 31, which is required in accordance with the increased amount of external air, with an intensity of ultraviolet light emitted to the ceramic filter 31 that is before the air volume is increased.

Therefore, in order to increase the air purification performance of the ceramic filter 31, it is required to increase the intensity of ultraviolet light emitted to the ceramic filter 31 in response to an increase in the air volume of the blower 40. In response to receiving a mode change command to increase an air amount of the blower 40, the controller according to the disclosed embodiment may increase a current value applied to the ultraviolet light emitter 32 so as to increase the air purification performance of the ceramic filter 31.

Further, in response to a command to change the second mode to the first mode, which is a command to reduce the air volume of the blower 40, being input through the inputter, the controller reduces a current value applied to the ultraviolet light emitter 32.

In response to receiving the command to change the second mode to the first mode, the controller may reduce the second current value, which is applied to the ultraviolet light emitter 32 in accordance with the second mode, to the first current value, which is applied to the ultraviolet light emitter 32 in accordance with the first mode. For example, the controller may apply the second current value of 200 mA to the ultraviolet light emitter 32 in the second mode, and in response to the first mode changed from the second mode, the controller may apply a current, which is reduced to the first current value of 50 mA, to the ultraviolet light emitter 32.

As the air volume of the blower 40 is reduced, the amount of external air introduced per a reference time is reduced. Therefore, due to the intensity of ultraviolet light emitted to the ceramic filter 31 that is before the air volume is reduced, it provides unnecessarily high air purification performance in comparison with the required air purification performance of the ceramic filter 31 in accordance with the reduced amount of the external air. Accordingly, it may cause waste of power.

Therefore, in response to the reduction in the air volume of the blower 40, it may be required to reduce the intensity of ultraviolet emitted from the ultraviolet light emitter 32 to the ceramic filter 31 so as to reduce the air purification performance of the ceramic filter 31. In response to receiving a mode change command to reduce the air volume of the blower, the controller according to the disclosed embodiment reduces the air purification performance of the ceramic filter 31 by reducing the current value applied to the ultraviolet light emitter 32.

As described above, the electronic device according to the disclosed embodiment may vary the air purification performance of the ceramic filter 31 by adjusting the current value applied to the ultraviolet light emitter 32 in response to the change in the air volume of the blowing device 40.

In addition, the clothes care apparatus according to the disclosed embodiment may control the current value applied to the ultraviolet light emitter 32 and the operation time in response to the temperature of the air introduced by the blower 40, and thus the clothes care apparatus may secure the life and reliability of the ultraviolet light emitter 32.

Figure 10:
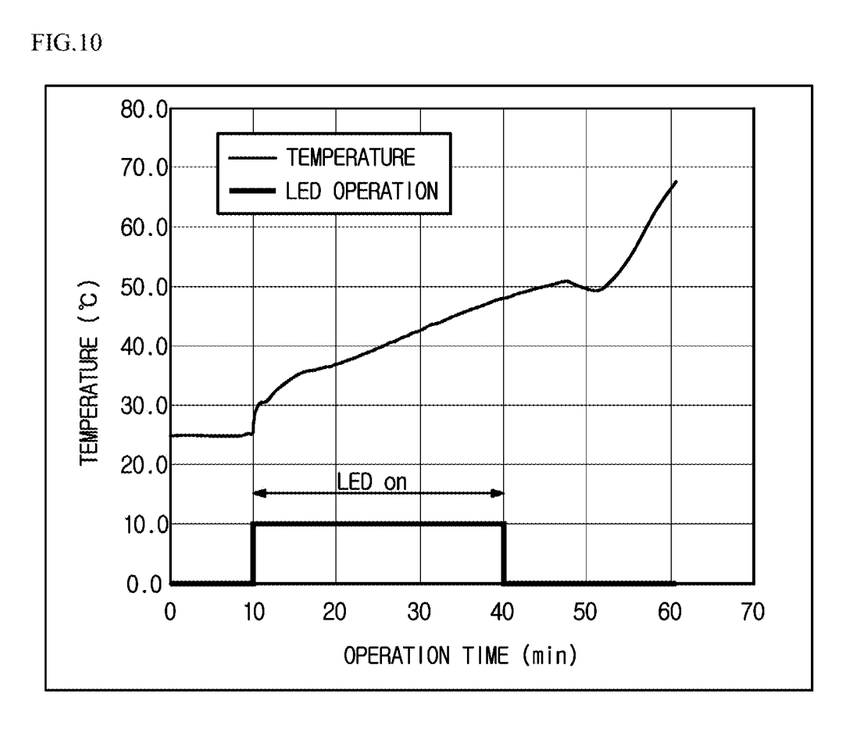
FIG. 10 is a graph illustrating an operation algorithm of the ultraviolet light emitter according to one embodiment of the present disclosure.

FIG. 10 is a graph illustrating an operation algorithm of the ultraviolet light-emitter according to one embodiment of the present disclosure.

In response to the current applied to the ultraviolet light emitter 32 that is an operation mode is secured for at least 10 minutes, it is possible to efficiently remove dust and odors inside the clothes care apparatus. On the other hand, as the operation time of the operation mode is increased, a lighting time of the ultraviolet light emitter 32 is increased, and it causes a reduction in the life of the ultraviolet light emitter 32. Accordingly, in the disclosure, the operation time of the ultraviolet light emitter 32 is adjusted to a range of from 10 to 60 minutes.

On the other hand, in response to applying the current to the ultraviolet light emitter 32 in a state in which the temperature of the air introduced by the blower 40 is excessively high, it is difficult to secure the life and reliability of the ultraviolet light emitter 32. Accordingly, the clothes care apparatus according to another aspect of the present disclosure may further include a temperature sensor (not shown).

Referring to FIG. 10, in response to the temperature of air sensed by the temperature sensor being higher than 70° C., the controller may secure the life and reliability of the ultraviolet light emitter 32 by blocking a current applied to the ultraviolet light emitter.

Hereinafter the present disclosure will be described in more detail with an embodiment.

The following Table 3 represents results of a comparative experiment between the clothes care apparatus employing the ceramic filter 31 according to the disclosed embodiment and a clothes care apparatus employing a conventional activated carbon filter.

Data shown in the table shows that there is a difference in a filter used as a deodorizing filter such as the ceramic filter 31 and the activated carbon filter, and other conditions except for the deodorization technology such as the blower 40 are performed under the same conditions. A test method is evaluated in accordance with the current domestic KS test method for performance of clothes care machine.

TABLE 3

| Number of repetitions | Conventional activated carbon deodorizing device | Ceramic catalyst according to the disclosure |
|---|---|---|
| 0 | 90% | 95% |
| 1 | 85% | 94% |
| 2 | 82% | 93% |
| 3 | 78% | 94% |
| 4 | 76% | 94% |
| 5 | 72% | 94% |
| 6 | 65% | 93% |
| 7 | 60% | 95% |
| 8 | 52% | 95% |

Referring to Table 3, it can be seen that the clothes care apparatus, to which the ceramic filter 31 according to the disclosed embodiment is applied, has an advantage in performance as the number of repetitions is increased. That is, it can be seen that the clothes care apparatus, to which the ceramic filter 31 according to the disclosed embodiment is applied, may be used semi-permanently.

The clothes care apparatus according to the disclosed embodiment may increase the service life and ease the off-flavor difficulty by independently configuring the ceramic filter having a mechanism of chemical decomposition, and the clothes care apparatus may improve the high temperature/high humidity reliability of UV-LEDs by installing the UV-LEDs on the outside of the flow path.

While the present disclosure has been particularly described with reference to exemplary embodiments, it should be understood by those of skilled in the art that various changes in form and details may be made without departing from the spirit and scope of the present disclosure.

INDUSTRIAL AVAILABILITY

The ceramic filter having a mechanism of chemical decomposition according to the embodiments of the present disclosure may be used semi-permanently, be not affected by humidity, and ease an off-flavor difficulty, and thus be applied to a clothes care apparatus.

The invention claimed is:

1. A clothes care apparatus comprising:
a blower to cause air to flow;
a flow path through which the air caused to flow by the blower moves; and
a deodorization module configured to purify the air caused to flow by the blower,
wherein
the deodorization module includes:
a ceramic filter provided inside the flow path, and
an ultraviolet light emitter outside of the flow path and facing the ceramic filter, and configured to emit ultraviolet light having an intensity corresponding to a current that is applied to the ultraviolet light emitter and that is adjustable in accordance with an intensity of air volume caused to flow by the blower,
the ceramic filter includes a base material and a catalyst applied on a surface of the base material,
a density of the base material is 0.5 g/ml to 3.0 g/ml and a moisture content of the base material is 5% or less,
the catalyst includes a photocatalyst or a thermal catalyst, and
the deodorization module is configured so that a flow rate of air passing through the ceramic filter is adjustable to 0.5 to 3.0 m/see to obtain a catalytic efficiency being 80% or more.

2. The clothes care apparatus of claim 1, wherein the deodorization module further includes:
a supporter configured to support the ultraviolet light emitter so that the ultraviolet light emitter is spaced apart from the ceramic filter by a predetermined distance.

3. The clothes care apparatus of claim 2, wherein the supporter is formed of at least one material of Poly(methyl methacrylate), polycarbonate, glass, and aluminum.

4. The clothes care apparatus of claim 2, wherein the supporter has a thickness of 1 to 2 mm.

5. The clothes care apparatus of claim 1, wherein the base material is formed of at least one of cordierite and mullite.

6. The clothes care apparatus of claim 5, wherein the catalyst consists of at least one of titanium oxide (TiO2), tungsten oxide (WO3), zinc oxide (ZnO), manganese dioxide (MnO2), or titanium tetraisopropoxide (TTIP).

7. The clothes care apparatus of claim 5, wherein the catalyst consists of at least one metal of Mn, Cu, Co, Pt, and Au.

8. The clothes care apparatus of claim 5, wherein the base material is formed in a honey-comb type having 100 to 300 pixels per inch.

9. The clothes care apparatus of claim 5, wherein the base material is formed in a porous foam type having 15 to 20 pixels per inch.

10. The clothes care apparatus of claim 1, wherein a distance between the ceramic filter and the ultraviolet light emitter is 10 mm or more and 25 mm or less.

11. The clothes care apparatus of claim 1, wherein a thickness of the ceramic filter is 5 mm or more and 15 mm or less.

12. The clothes care apparatus of claim 1, wherein the ultraviolet light emitter is configured so that the current applied to the ultraviolet light emitter is adjustable in a range from 50 to 200 mA.

13. The clothes care apparatus of claim 1, wherein the ultraviolet light emitter is configured so that an operation time of the ultraviolet light emitter is adjustable in a range from 10 to 60 minutes.

14. The clothes care apparatus of claim 1, wherein the ultraviolet light emitter is configured so that, in response to a second mode in which an intensity of air volume caused to flow by the blower is stronger than an intensity of air volume caused to flow by the blower in a first mode, the current applied to the ultraviolet light emitter is increased to be greater than the current applied to the ultraviolet light emitter in the first mode.

15. The clothes care apparatus of claim 1, wherein the ultraviolet light emitter is configured so that the current applied to the ultraviolet light emitter is adjustable in accordance with a temperature of air caused to flow by the blower to secure life and reliability of the ultraviolet light emitter.

16. The clothes care apparatus of claim 1, wherein the ultraviolet light emitter is configured so that the current applied to the ultraviolet light emitter is blocked in response to a temperature of air cause to flow by the blower being higher than 70° C.

17. The clothes care apparatus of claim 1, wherein the deodorization module further includes:
a dust collecting filter at a front end of the ceramic filter.

* * * * *